United States Patent [19]

Milgrom

[11] 4,384,587
[45] May 24, 1983

[54] SPATULA FOR COLLECTING CERVICAL CANCER CELLS

[75] Inventor: Hymen Milgrom, Chicago, Ill.

[73] Assignee: Milex Products, Inc., Chicago, Ill.

[21] Appl. No.: 178,995

[22] Filed: Aug. 18, 1980

[51] Int. Cl.³ .............................................. A61B 10/00
[52] U.S. Cl. .................................... 128/757; 128/304; 128/758
[58] Field of Search ......................... 128/757, 758, 304

[56]    References Cited
U.S. PATENT DOCUMENTS

| | | | |
|---|---|---|---|
| 2,049,956 | 8/1936 | Greenberg | 128/304 |
| 2,437,329 | 3/1948 | Moore | 128/304 X |
| 3,352,299 | 11/1967 | Sagiroglu | 128/304 X |
| 3,633,565 | 1/1972 | McDonald | 128/304 X |
| 3,635,222 | 1/1972 | Robinson | 128/304 |

FOREIGN PATENT DOCUMENTS 705401  6/1931  France ............................... 128/304

*Primary Examiner*—Kyle L. Howell
*Assistant Examiner*—Nancy A. B. Swisher

*Attorney, Agent, or Firm*—Wallenstein, Wagner, Hattis, Strampel & Aubel

[57]    ABSTRACT

A spatula for collecting cancer cells outside and within the cervix canal includes a scraper head having a laterally extending outer cervix engaging leg projecting from one side of the head. The head further includes a cervical canal entering finger-like portion projecting longitudinally beyond the leg. The finger-like portion has on the same side of the scraping head from which said leg projects a longitudinal inner scraping surface which scrapes cells from the wall of the cervical canal when the spatula is rotated along the longitudinal axis of the spatula. The longitudinal inner surface of the finger-like portion comprises two adjacent longitudinally extending sections, one of which has a rough surface which scrapes cells from the wall of the cervical canal and the other of which has a relatively smooth surface. The smooth surface section is raised so that only it engages the wall of the cervix during the longitudinal movement of the finger-like portion of the scraping head into and out of the cervical canal.

7 Claims, 6 Drawing Figures

U.S. Patent   May 24, 1983   4,384,587
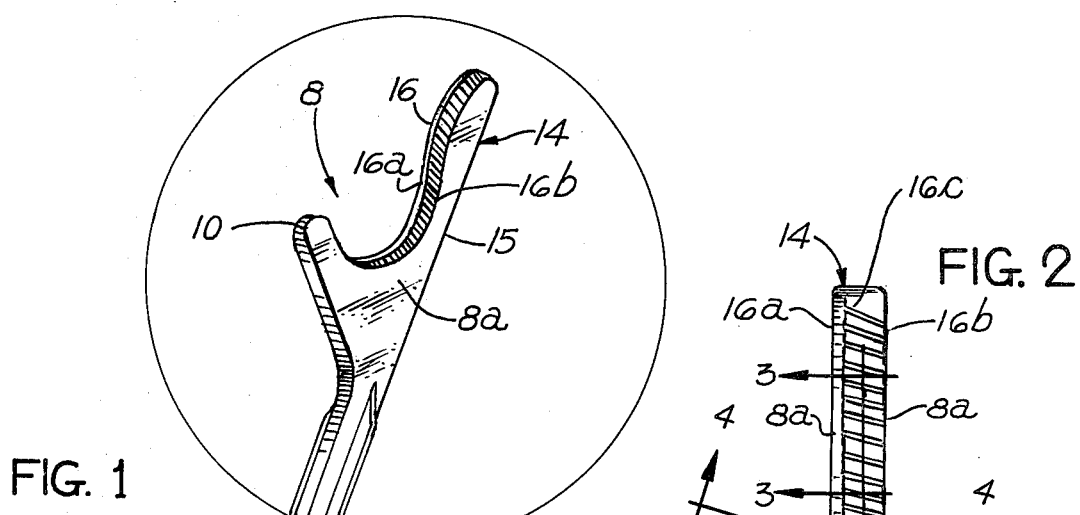
FIG. 1
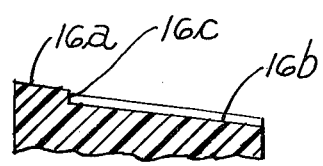
FIG. 2
FIG. 3
FIG. 4
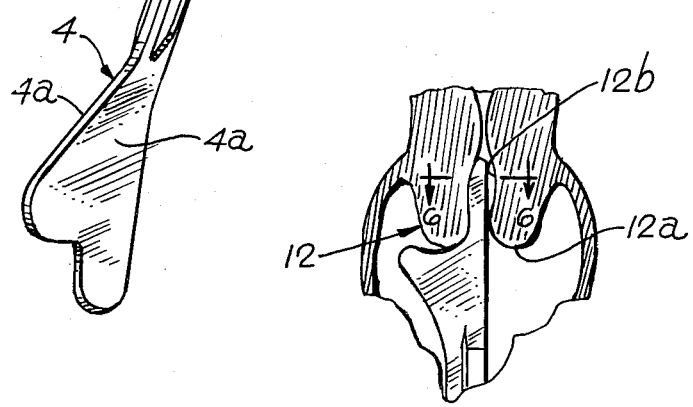
FIG. 5
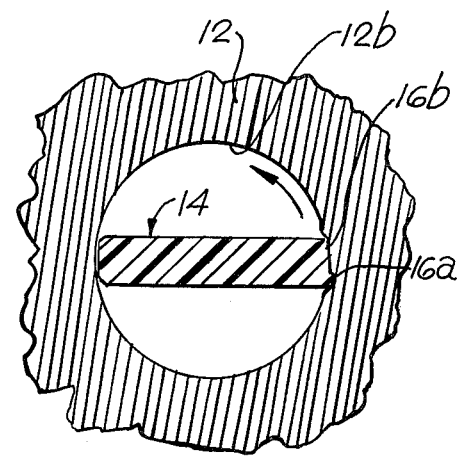
FIG. 6

SPATULA FOR COLLECTING CERVICAL CANCER CELLS

BACKGROUND OF INVENTION

The present invention relates to devices called spatulas used by a physician for collecting cancer cell specimens within the cervical canal and the cervical os. These devices have been heretofore manufactured in a form having a long straight insertion handle terminating in a scraping head comprising a laterally extending positioning leg which limits the insertion depth of a finger-like portion extending longitudinally beyond this leg and positioned in alignment with the handle of the device. These devices are generally made of wood or synthetic plastic material and are sold in sterilized packages at a cost where they are used only once. The finger-like portion of the scraping head is inserted by the physician into the cervical canal as far as the positioning leg will permit, and as a scraping surface on the inner leg-containing side of the finger-like portion thereof is urged against the cervical canal the device is rotated along its longitudinal axis so that the inner longitudinal side of the finger-like portion and the positioning leg of the scraping head collect cell specimens. The cells are transferred to a test slide for microscope examination by tapping and sliding the scraping head against the slide.

In the wooden spatula, the wood is porous and some of the cells and fluid collected are absorbed by the porous wooden surface on the scraping side of the scraping head. It was found that these spatulas have a limited scraping action since the surface of the scraping side of the scraping head is not of sufficient roughness for efficient scraping of surface cells which are especially meaningful to the cytologist reading slides of such specimen. Also, because of the porous nature of the spatulas, cells which are absorbed by the porous wooden surfaces thereof are not easily transferred to a test slide and frequently remain on or in the pores of the scraping heads thereof.

The synthetic plastic spatulas were made with grooves in scraping surface of the spatula, which grooves formed pockets for collecting cell specimens which are very readily transferable to the test slides. Because of the narrowness of the scraping surfaces utilized, the grooves were formed in a lateral direction to form a large number of open-ended grooves which provide a better collection and transfer of cell specimens to the test slides. However, the resulting sawtooth-like profile, in the process of longitudinally inserting and removing the scraping head into and from the cervical canal, frequently ruptures surface blood vessels which can cause discomfort and some minor bleeding which results in blood in the cell samples which hinders examination of the cell specimens on the test slide to which the cell samples are transferred and results in needless bleeding of the patient. For these reasons, the physician using this spatula is instructed to press the smooth backside of the scraping head against the cervical canal during the insertion and removal of the spatula from the cervix. Not infrequently, however, the doctor fails to do this and the undesired blood appears with the collected cell specimens. Also in case of a very tight cervical canal it may not be possible for the physician to press down sufficiently on the smooth backside of the scraping head as per instructions and the grooves come in direct contact with the tissue during insertion and removal and as a result traumatize the cervix and make it difficult if not impossible to avoid bleeding.

It is acccordingly one of the objects of the present invention to provide an improved spatula for collecting cell specimens from the cervical canal which does not have the disadvantages of the prior spatulas above described.

SUMMARY OF THE INVENTION

The spatula of the present invention utilizes a rough preferably grooved inner longitudinal scraping surface on the scraping head of the spatula for collecting cell specimens and readily transferring the same to a glass slide, but without the serious risk of rupturing blood vessels during the insertion and withdrawal of the spatula from the cervical canal, even when the physician does not or cannot press the smooth backside of the spatula against the cervical canal wall during spatula insertion and withdrawal. Accordingly, no such special insertion or removal procedures are needed. To this end, the inner longitudinal scraping surface of the scraping head comprises two separate longitudinally extending sections, one being raised or outermost smooth portion which engages the cervical wall during the longitudinal movement of the spatula into and out of the cervical canal, and an inner or lower preferably groove longitudinally extending section which acts as the scraping surface for the scraping head of the spatula when it is pressed against the cervical canal wall during rotation of the spatula in a direction where the smooth surfaced longitudinal section is on the trailing side of the rotating scraping head. The grooved longitudinal section of the scraping head is preferably inclined in a plane angled in a lateral direction so that the grooved section will face and contact the cervical wall during such rotation of the spatula.

Another feature of the invention useful also on prior spatula designs is the provision of a step on the trailing, raised side of the rotating scraping head which forms a specimen-collecting shoulder which keeps the specimen on the spatula during the rotation thereof. The prior spatulas did not have this shoulder, and so some of the specimen material leaked off the spatula as it was rotated within the cervical canal.

DESCRIPTION OF DRAWINGS

FIG. 1 is a perspective view of the spatula of the invention with the scraping head thereof viewed through a magnifying glass;

FIG. 2 is a fragmentary plan view of the scraping head of the spatula shown in FIG. 1, locking down on the scraping surface thereof;

FIG. 3 is an enlarged fragmentary longitudinal sectional view through the scraping surface of the scraping head of the spatula of FIG. 2, as seen along section line 3—3 therein;

FIG. 4 is an enlarged transverse sectional view through the scraping surface of the scraping head in the viewing plane 4—4 shown in FIG. 2, which plane extends parallel to the grooves therein;

FIG. 5 is a full scale view showing the insertion of the scraping head of the spatula of FIGS. 1 through 4 into the cervical canal; and FIG. 6 is a greatly enlarged transverse sectional view through the spatula in the cervical canal shown in FIG. 5, taken along section line 6—6 therein.

DESCRIPTION OF EXEMPLARY FORM OF THE INVENTION SHOWN IN THE DRAWINGS

Referring now more particularly to FIG. 1, the spatula of the invention there shown is a device preferably made of any suitable synthetic plastic material and including a handle 4 connected by a shank 6 to a scraping head 8. The handle is shown as being flat and narrow and having parallel flat side faces 4a—4a which can be conveniently gripped and to provide the physician with planes of reference so that he knows at all times the orientation of the scraping head 8 which has a pair of flat side faces 8a—8a which are parallel to the side faces 4a—4a of the handle.

The scraping head includes a laterally extending leg 10 which, as shown in FIG. 5, engages the outer surface 12a of the cervix 12, thereby limiting the depth of insertion of the scraping head into the cervical canal 12b. The scraping head includes a longitudinally extending scraping finger 14 which is preferably in alignment with the shank 6 of the spatula. The scraping finger 14, which is sufficiently narrow as to readily enter the cervical canal, has an outer, longitudinally extending face or side 15 which has a smooth surface, and an inner longitudinally extending scraping face or side 16 which merges with the inner face or side of the leg 10 of the scraping head which also acts as a scraping surface. The inner face or side 16 of the finger 14 comprises a raised, smooth, longitudinally extending section 16a preferably of very narrow extent, and a much wider, lower, rough surface, longitudinally extending scraping section 16b. The raised section 16a joins the scraping section 16b at a step 16c which forms a specimen collection shoulder as previously described. The lower, rough surfaced section 16b generally extends along a plane inclined in a lateral direction. The raised smooth section 16a is located a greater distance from the longitudinal axis of the spatula than the lower rough surfaced section 16b, so that only the smooth section will contact the cervical canal walls as the spatula scraping head is moved longitudinally into and out of the cervical canal. This eliminates the problem of tissue damage and bleeding.

The rough surface of the lower longitudinally extending section 16b of the finger 14 is preferably formed by similar longitudinally spaced laterally extending grooves 18 which are inclined slightly with respect to a line transverse to the longitudinal axis of the spatula to enhance the cell scraping action of the scraping head. This grooved section 16b merges with a similarly grooved inner face 10b of the leg 10, so that cell specimens are collected both from the cervical canal and the outer surface of the cervix. It can be appreciated that, with the illustrated inclination of the lower grooved section 16b of the finger 14, a clockwise rotation imparted to the spatula viewed from the handle end of the spatula places the smooth section 16a thereof on the trailing side of the rotating scraping head so that the grooved inner urged section 16b of the finger 10 of the scraping head section 16b faces and scrape cells from the cervix, as best shown in FIG. 6.

The present invention thus has the advantage of having on the scraping head a rough surface, preferably formed by collecting grooves 18 for readily collecting cancer cells during the scraping process described, without any appreciable risk of cutting the cervical wall 12b during the longitudinal insertion and removal of the spatula from the cervical canal.

It should be understood that numerous modifications may be made in the scraping head described without deviating from the broader aspects of the invention.

I claim:

1. In a spatula for collecting cancer cells within the cervical canal, said spatula including a handle portion to be gripped by the physician, a shank extending longitudinally from the handle portion, and a scraping head at the end of the shank, a scraping head including a cervical canal entering finger-like portion having a longitudinal inner surface which is to scrape cells from the wall of the cervical canal when the spatula is rotated along the longitudinal axis of the spatula, the improvement wherein said longitudinal inner surface of the finger-like portion of said scraping head comprises two adjacent side-by-side longitudinally extending sections, one of which has a rough surface which scrapes cells from the wall of the cervical canal, and the other of which has a relatively smooth surface, said rough surface section being located closer to the longitudinal center axis of said finger-like portion than said smooth surface section, so that said smooth section rather than said rough surface section thereof engages the wall of the cervix during the longitudinal movement of the finger-like portion into and out of the cervical canal, and said rough surface section engaging the walls of the cervical canal to scrape cells therefrom when the inner side of the head is pressed against the cervical canal wall and the spatula is rotated about its longitudinal axis in a direction where said smooth surface section is on the trailing side of the rotating head.

2. In a spatula for collecting cancer cells within the cervical canal, said spatula including a handle portion to be gripped by the physician, a shank extending longitudinally from the handle portion, and a scraping head at the end of the shank, and scraping head having a laterally extending leg projecting from one side of the head which leg is adapted to engage the outer surface of the cervix and a cervical canal entering finger-like portion projecting longitudinally beyond said leg, which finger-like portion has on the same side of the head from which said leg projects a longitudinal inner surface which is to scrape cells from the wall of the cervical canal when the spatula is rotated along the longitudinal axis of the spatula, the improvement wherein said longitudinal inner surface of the finger-like portion of said head comprises to adjacent side-by-side longitudinally extending sections, one of which has a rough surface which merges with a rough inner surface of said leg so that the inner sides of said finger-like portion and leg of said head scrape cells from the inner and outer surfaces of the cervix, the other longitudinal section of said finger-like portion having a relatively smooth surface, said rough surface section of the finger-like portion being located closer to the center axis of the finger than said smooth surface section thereof so that said smooth surface section rather than said rough surface section thereof engages the wall of the cervix during the longitudinal movement of the finger-like portion of the head into and out of the cervical canal, and said rough surface longitudinal section engaging the wall of the cervical canal to scrape cells therefrom when the inner leg containing side of the head is pressed against said cervical canal wall and the spatula is rotated about its longitudinal axis in a direction where said smooth surface longitudinal section is on the trailing side of the rotating head.

3. The spatula of claim 1 or 2 wherein the rough surface longitudinal section of the inner side of the finger-like portion of the scraping head is in a laterally inclining plane.

4. The spatula of claim 1 or 2 wherein said rough longitudinal surface of the finger-like portion of the scraping head is formed by laterally extending grooves.

5. The spatula of claim 1 or 2 wherein said rough longitudinal surface of the finger-like portion of the scraping head is formed by laterally extending grooves which also incline with respect to a line extending transversely to the longitudinal axis of the spatula, to increase the scraping action thereof.

6. The spatula of claim 1 or 2 wherein said smooth section of said scraping head joins said rough surface section along a step formed in the scraping head, which step forms a collection shoulder for the collected specimen as the spatula is rotated within the cervical canal, thereby inhibiting leakage of the specimen material as the spatula is rotated in a given direction within the cervical canal.

7. A spatula of claim 1 wherein said finger-like portion has flat parallel side faces extending between said longitudinal face and said longitudinal inner surface thereof.

* * * * *